United States Patent
Hopkins

(10) Patent No.: US 10,874,407 B2
(45) Date of Patent: Dec. 29, 2020

(54) BONE DEPTH STOP APPARATUS AND METHOD

(71) Applicant: Zimmer, Inc., Warsaw, IN (US)

(72) Inventor: Andrew Hopkins, Winterthur (CH)

(73) Assignee: Zimmer, Inc., Warsaw, IN (US)

( * ) Notice: Subject to any disclaimer, the term of this patent is extended or adjusted under 35 U.S.C. 154(b) by 512 days.

(21) Appl. No.: 15/159,069

(22) Filed: May 19, 2016

(65) Prior Publication Data
US 2016/0345988 A1 Dec. 1, 2016

Related U.S. Application Data

(60) Provisional application No. 62/166,976, filed on May 27, 2015.

(51) Int. Cl.
*A61B 17/16* (2006.01)
*A61B 90/00* (2016.01)

(52) U.S. Cl.
CPC ...... *A61B 17/1659* (2013.01); *A61B 17/1684* (2013.01); *A61B 90/03* (2016.02); *A61B 2090/036* (2016.02)

(58) Field of Classification Search
CPC ............ A61B 17/1659; A61B 17/1664; A61B 17/1675; A61B 17/1684; A61B 90/03; A61B 2090/039; A61B 2090/067
USPC ....................................................... 606/102
See application file for complete search history.

(56) References Cited

U.S. PATENT DOCUMENTS

| | | | | |
|---|---|---|---|---|
| 4,777,942 A | * | 10/1988 | Frey | A61B 17/175 409/178 |
| 6,224,605 B1 | * | 5/2001 | Anderson | A61B 17/15 606/85 |
| 2002/0058948 A1 | * | 5/2002 | Arlettaz | A61B 17/1725 606/98 |
| 2005/0107802 A1 | * | 5/2005 | Vanasse | A61B 5/1076 606/102 |
| 2007/0093844 A1 | * | 4/2007 | Dye | A61B 17/1659 606/84 |
| 2009/0270875 A1 | * | 10/2009 | Poncet | A61B 17/164 606/102 |
| 2012/0035612 A1 | * | 2/2012 | Green | A61B 17/1746 606/102 |

* cited by examiner

*Primary Examiner* — Matthew J Lawson
(74) *Attorney, Agent, or Firm* — Schwegman Lundberg & Woessner, P.A.

(57) ABSTRACT

An instrument can comprise an instrument body, a cross-pin, and a ring. The instrument body can be configured to be partially inserted into an intramedullary canal of a bone having a bone resection. The cross-pin can extend through the instrument body, and the ring can be movably coupled to the cross-pin and positionable on the bone resection. The ring can be configured to pivot about a longitudinal axis of the cross-pin such that an angle of the ring relative to the instrument body approximates a surface angle of the bone resection relative to the instrument body. Additional apparatus, methods, and systems are disclosed.

19 Claims, 5 Drawing Sheets

BONE DEPTH STOP APPARATUS AND METHOD

RELATED APPLICATIONS

This applications claims the benefit of priority to U.S. Provisional Application Ser. No. 62/166,976, filed May 27, 2015, the content of which is hereby incorporated by reference in its entirety.

BACKGROUND

Some orthopedic procedures for the replacement of all, or a portion of, a patient's joint, such as hip, knee, shoulder, and elbow arthroplasty procedures, include forming a canal in the bone within which to seat a portion of the artificial joint implant. Such bones typically include a hardened outer layer of compact bone surrounding an inner layer of spongy bone and/or marrow. Instruments such as reamers and rasps can be used by surgeons to form and size the canal by removing marrow and spongy bone along a length of the bone sufficient to accept the portion of the implant. It is important that practitioners avoid removing too much spongy bone, however, and forming too large of a canal for the intended implant. Being overly aggressive in rasping the spongy bone, for instance, can result in the removal of the spongy bone all the way down to the compact bone, which, in turn, can result in an oversized channel.

Overview

To better illustrate the instrument disclosed herein, a non-limiting list of examples is provided here:

In Example 1, an instrument can be provided that includes an instrument body configured to be partially inserted into an intramedullary canal of a bone having a bone resection, a cross-pin extending through the instrument body, and a ring movably coupled to the cross-pin and positionable on the bone resection, the ring configured to pivot about a longitudinal axis of the cross-pin such that an angle of the ring relative to the instrument body approximates a surface angle of the bone resection relative to the instrument body.

In Example 2, the instrument of Example 1 is optionally configured such that the instrument body comprises a rasp handle.

In Example 3, the instrument of any one of or any combination of Examples 1-2 is optionally configured such that the instrument body further comprises a rasp, such that the rasp is configured to be inserted into the intramedullary canal of the bone.

In Example 4, the instrument of any one of or any combination of Examples 1-3 is optionally configured such that the instrument body comprises an implant stem or a trial stem.

In Example 5, the instrument of any one of or any combination of Examples 1-4 is optionally configured such that the ring comprises a first portion and a second portion, the first and second portions being configured for assembly on the cross-pin to form the ring.

In Example 6, the instrument of any one of or any combination of Examples 1-5 is optionally configured such that the ring comprises metal.

In Example 7, the instrument of any one of or any combination of Examples 1-6 is optionally configured such that the ring comprises plastic.

In Example 8, the instrument of any one of or any combination of Examples 1-7 is optionally configured such that the instrument further comprises an inclination indicator, configured to indicate the surface angle of the bone resection when the ring is positioned on the bone resection.

In Example 9, the instrument of Example 8 is optionally configured such that the inclination indicator comprises markings on the instrument body.

In Example 10, the instrument of any one of or any combination of Examples 1-9 is optionally configured such that the instrument comprises a depth stop system for shoulder replacement surgery.

In Example 11, the instrument of any one of or any combination of Examples 1-10 is optionally configured such that the ring prevents the instrument body from being inserted into the intramedullary canal of the bone beyond a predetermined depth.

In Example 12, an instrument can be provided that includes an instrument body configured to be partially inserted into an intramedullary canal of a bone having a bone resection, a cross-pin extending through the instrument body, and a ring attached to the cross-pin, the ring configured to rotate about a longitudinal axis of the cross-pin such that when a base surface of the ring contacts a surface of the bone resection, the instrument body is prevented from being inserted into the intramedullary canal of the bone beyond a predetermined depth.

In Example 13, the instrument of Example 12 is optionally configured such that the instrument body comprises a rasp handle.

In Example 14, the instrument of any one of or any combination of Examples 12-13 is optionally configured such that the instrument comprises a depth stop system for shoulder replacement surgery.

In Example 15, the instrument of any one of or any combination of Examples 12-14 is optionally configured such that when a base surface of the ring contacts a surface of the bone resection, an angle of the ring relative to the instrument body approximates a surface angle of the bone resection relative to the instrument body.

In Example 16, the instrument of any one of or any combination of Examples 12-15 is optionally configured such that the ring is integral with the cross-pin, such that the cross-pin rotates about its longitudinal axis with the ring.

In Example 17, a method can be provided that includes inserting a cross-pin through an opening in an instrument body, and attaching a ring to the cross-pin, such that the ring encircles the instrument body, the ring configured to pivot about the cross-pin such that an angle of the ring relative to the instrument body can approximate a surface angle of a bone resection relative to the instrument body.

In Example 18, the method of Example 17 optionally includes attaching the ring to the cross-pin by coupling a first portion of the ring to a second portion of the ring, and coupling the cross-pin to at least one of the first portion and the second portion.

In Example 19, the method of any one of or any combination of Examples 17-18 optionally includes inserting the cross-pin through the opening in the instrument body by threadably coupling the cross-pin to the instrument body.

In Example 20, the method of any one of or any combination of Examples 17-19 optionally includes making a depth stop instrument for shoulder replacement surgery.

These and other examples and features of the present devices, systems, and methods will be set forth in part in the following Detailed Description. This overview is intended to provide a summary of subject matter of the present patent application. It is not intended to provide an exclusive or exhaustive removal of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

In a healthy shoulder, the proximal humerus is generally ball-shaped, and articulates within a socket formed by the scapula (sometimes referred to as a shoulder blade), called the glenoid, to form the shoulder joint. Some types of injury, disease, or degeneration can produce pain, restricted motion in the shoulder joint, or both. One treatment for certain types of damage to a shoulder joint is surgery. In some cases, the shoulder joint is surgically replaced. Shoulder surgery can include implantation of a humeral component having a stem that fits within an intramedullary canal of a resected humerus bone, and an articulating head that articulates within the socket of a glenoid component implanted within the glenoid of the scapula. A practitioner can form the intramedullary canal to a predetermined depth and determine an inclination angle of the bone resection in order to provide a proper fit for an implant. While the examples are described with reference to shoulder replacement surgery, the apparatus and methods can similarly be applied to any of a variety of orthopedic procedures.

Figure 1:
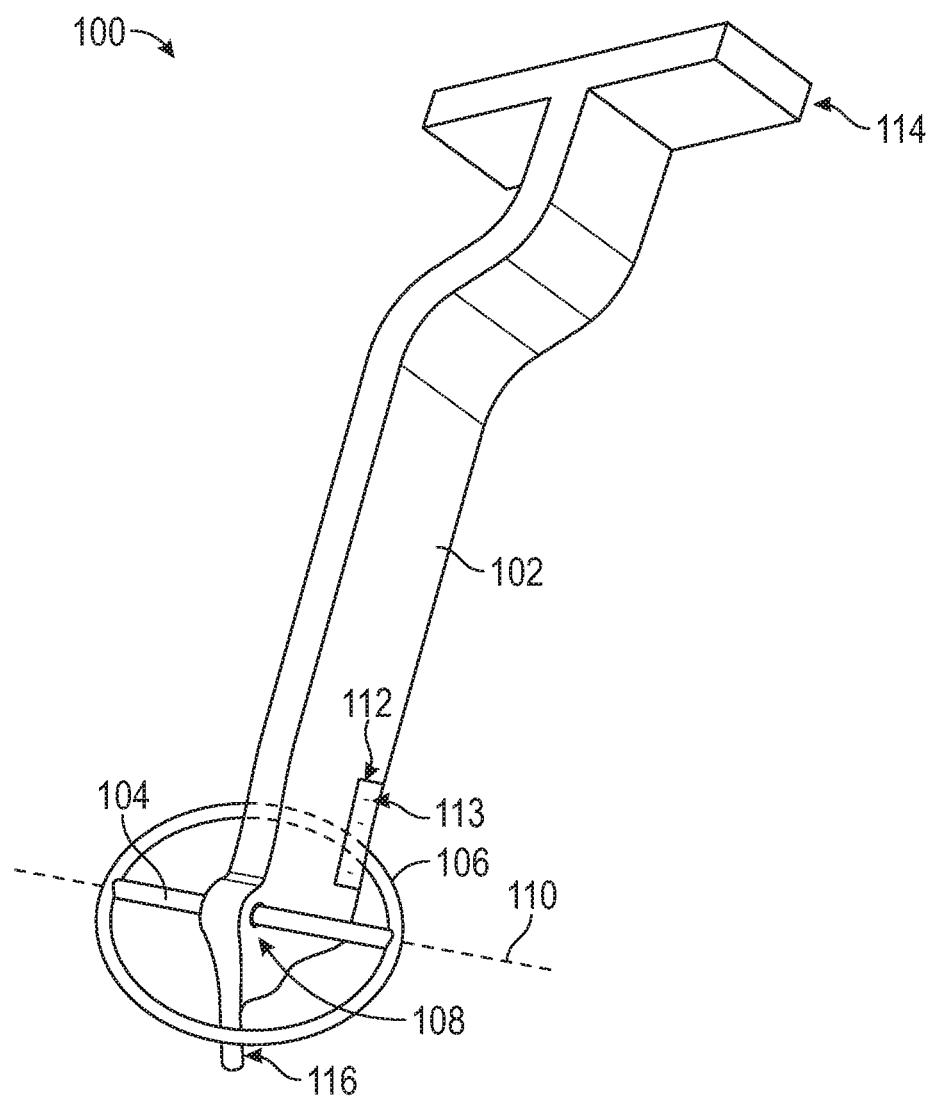
FIG. 1 is a perspective view of a depth stop instrument, in accordance with at least one example of the present disclosure.

FIG. 1 is a perspective view of a depth stop instrument 100, in accordance with at least one example of the present disclosure. The instrument 100 can comprise an instrument body 102, a cross-pin 104, and a ring 106. In at least one example, the cross-pin 104 can extend through the instrument body 102 via an opening 108 in the instrument body 102. The ring 106 can be configured to pivot about a longitudinal axis 110 of the cross-pin 104. For example, the ring 106 can be movably coupled to the cross-pin 104. In another example, the ring 106 is integral with the cross-pin 104 or is coupled to the cross-pin 104, such that as the ring 106 pivots about the longitudinal axis 110 of the cross pin, the cross-pin 104 rotates about its longitudinal axis 110 within the opening 108 in the instrument body 102.

In some examples, the depth stop instrument 100 can comprise an inclination indicator 112 to indicate an angle of the ring 106 as it pivots about the longitudinal axis 110. In the illustrated example, the inclination indicator 112 comprises markings 113 on the instrument body 102. In other examples, the inclination indicator 112 can comprise any of a variety of angle measurement mechanisms. In some examples, the inclination indicator 112 can comprise a lock to lock the ring 106 at a particular inclination angle. In such an example, the inclination indicator 112 can allow the ring 106 to be compared to, or otherwise used with, other surfaces at the locked inclination angle. In at least one example, the inclination indicator 112 is a separate instrument used in conjunction with the depth stop instrument 100 to determine an inclination angle associated with the ring.

In various examples, the instrument body 102 can be configured to be partially inserted into an intramedullary canal of a bone having a bone resection, and the ring 106 can be positionable on the bone resection. In at least one example, the instrument body 102 can comprise a rasp handle 114 and a rasp 116 to be inserted into the intramedullary canal. In such an example, the ring 106 can provide a depth stop for the instrument body 102 to prevent the rasp 116 from being inserted into the intramedullary canal beyond a predetermined depth. The ring 106 can provide a greater surface area than the cross-pin 104 alone, to help avoid damage to the bone during positioning or rasping. In at least one example, the cross-pin 104 does not come in contact with the bone resection when the ring 106 lays flat on the bone resection. In at least one example, the instrument body 102 can comprise an implant stem or a trial stem, such that the ring 106 can prevent the implant stem or trial stem from being inserted into the intramedullary canal deeper than a predetermined depth.

Figure 2:
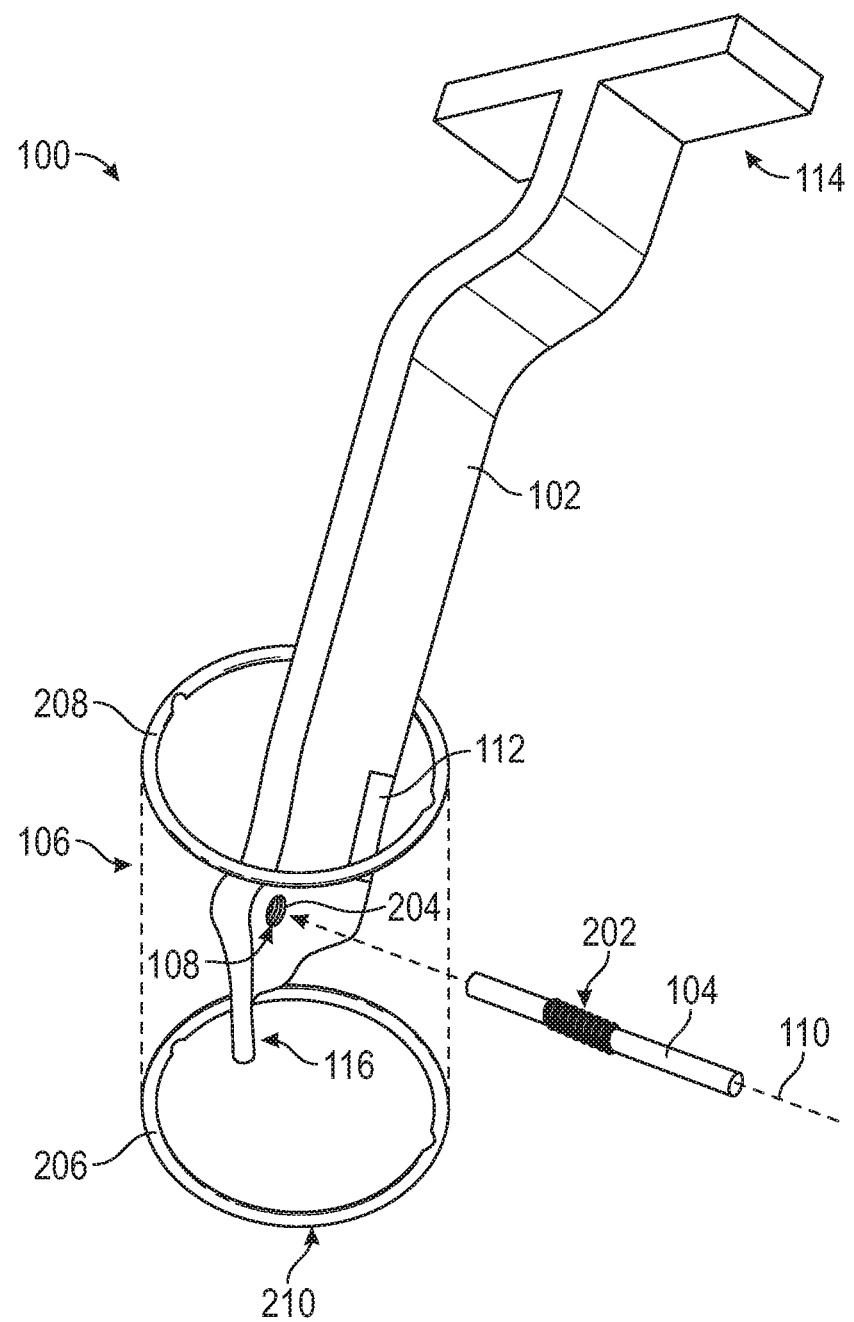
FIG. 2 is an exploded perspective view of a depth stop instrument, in accordance with at least one example of the present disclosure.

FIG. 2 is an exploded perspective view of the depth stop instrument 100, in accordance with at least one example of the present disclosure. In the illustrated example, instrument body 102 of the depth stop instrument 100 comprises a bent rasp handle 114 and a rasp 116. In other examples, the instrument body 102 can comprise any variety of rasp handles or rasps. For example, the instrument body 102 can comprise a straight rasp handle. In yet further examples, the instrument body 102 can comprise a trial stem or an implant stem.

The cross-pin 104 can be inserted into the instrument body 102, such that the cross-pin 104 extends through the instrument body 102. In at least one example, the cross-pin 104 is threadably coupled to the instrument body 102 via corresponding threads 202, 204. In another example, the cross-pin 104 is formed integral with the instrument body 102. In yet another example, the cross-pin is attached to the instrument body 102 using any of a variety of fasteners, for example adhesive, solder, screws, bolts, or the like.

In the illustrated example, the ring 106 is depicted as comprising a first portion 206 and a second portion 208, such that the first portion 206 and the second portion 208 can be assembled to form the ring 106. In at least one example, the first portion 206 and the second portion 208 can be assembled over the cross-pin 104 to form the ring 106. In another example, the ring 106 comprises a single portion, and the cross-pin 104 is coupled to the single portion of the ring 106. The ring 106 can be attached to the cross-pin 104 using any of a variety of fasteners, for example adhesive, solder, screws, bolts, or the like.

The ring 106 can be configured to rotate about the longitudinal axis 110 of the cross-pin 104. In at least one example, the ring 106 can pivot about the cross-pin 104. In another example, rotation of the ring 106 causes the cross-pin 104 to rotate about its longitudinal axis 110. In at least one example, a base surface 210 of the ring 106 is configured to contact a surface of a bone resection. For example, as the instrument body 102 is partially inserted into an intramedullary canal, the ring 106 can be configured to rotate about the longitudinal axis 110 of the cross-pin 104, such that the base surface 210 of the ring 106 comes in contact with the bone resection to provide a depth stop for the instrument body 102. The surface area of the base surface 210 of the ring 106 in contact with the bone resection can allow force to be applied to the instrument body 102 (for rasping or otherwise, as necessary for the orthopedic procedure) without damaging the bone. Further, when the base surface 210 of the ring 106 is substantially flush with the bone resection, the angle of the ring 106 relative to the instrument body 102 can approximate a surface angle of the bone resection relative to the instrument body 102. In at least one example, the inclination indicator 112 can measure the angle of the ring 106. In at least one example, the inclination indicator 112 in combination with the ring 106 can indicate the surface angle of the bone resection when the ring 106 is positioned on the bone resection.

In at least one example, one or more of the instrument body 102, the cross-pin 104, and the ring 106, comprises metal, for example, stainless steel. In at least one example, one or more of the instrument body 102, the cross-pin 104, and the ring 106, comprises plastic. In some examples one or more of the instrument body 102, the cross-pin 104, and the ring 106 comprises a combination of materials.

Figure 3:
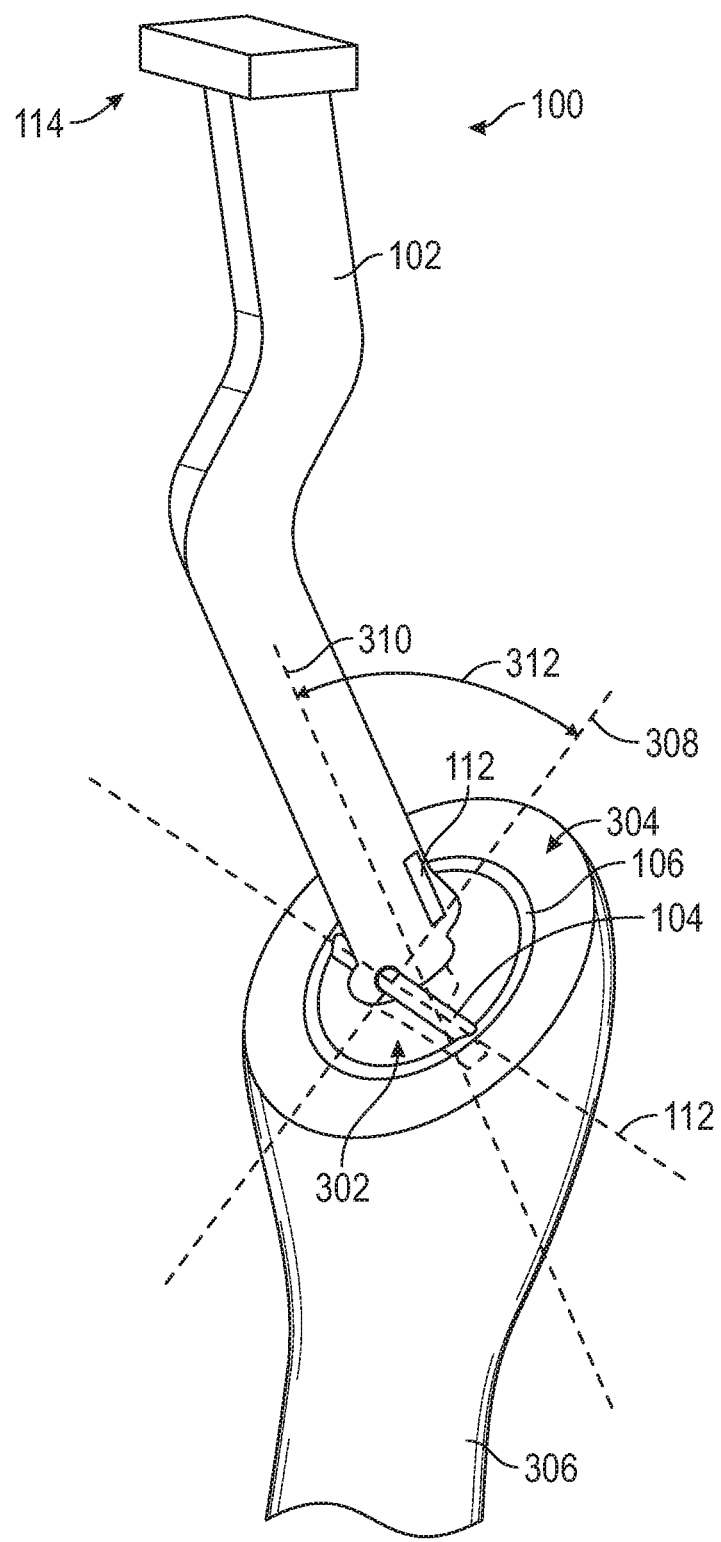
FIG. 3 is a perspective view of a depth stop instrument inserted into an intramedullary canal of a bone having a bone resection, in accordance with at least one example of the present disclosure.

FIG. 3 is a perspective view of the depth stop instrument 100 inserted into an intramedullary canal 302 of a bone 306 having a bone resection 304, in accordance with at least one example of the present disclosure. For example, in the context of shoulder replacement surgery, the bone resection 304 can be formed at the proximal end of the humerus bone 306, and the intramedullary canal 302 can extend from the surface of the bone resection 304 into the humerus bone 306.

In the illustrated example, the instrument body 102, comprising the rasp handle 114 and the rasp 116, is inserted into the intramedullary canal 302 until the bottom surface 210 of the ring 106 contacts the bone resection 304, preventing the instrument body 102 from inserting into the intramedullary canal 302 beyond a predetermined depth. With the bottom surface 210 of the ring 106 resting on the surface of the bone resection 304, the ring 106 and the surface of the bone resection 304 share a common axis 308. The common axis 308 can be compared to an additional axis 310, such as a longitudinal axis of the instrument body 102, to measure an angle 312 of the ring 106 that can be used to approximate an inclination angle of the surface of the bone resection 304. In some examples, the inclination angle can be determined using the inclination indicator 112. In at least one example, the location of the ring 106 is compared to the inclination indicator 112 to determine the inclination angle of surface of the bone resection 304.

Figure 4:
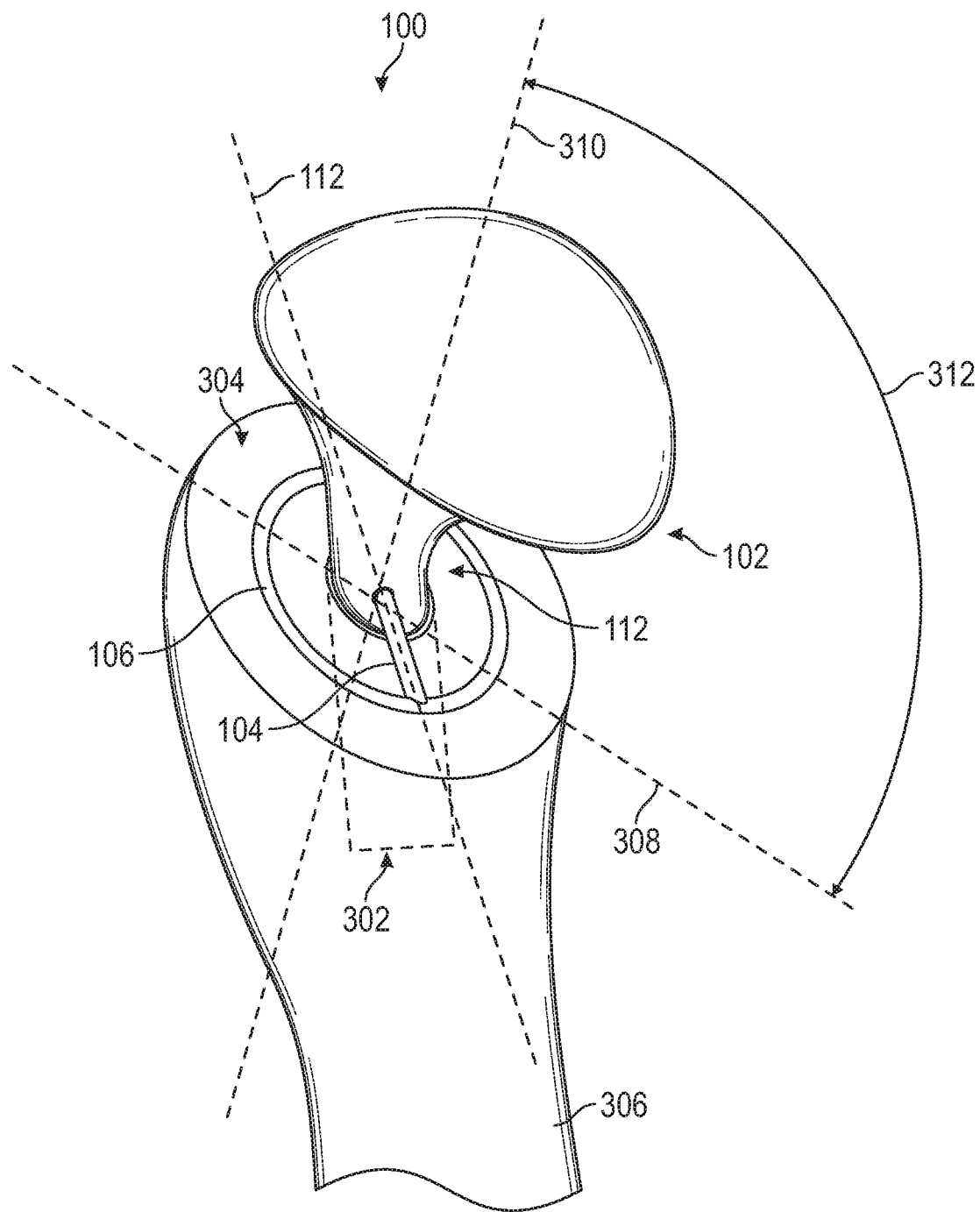
FIG. 4 is a perspective view of a depth stop instrument inserted into an intramedullary canal of a bone having a bone resection, in accordance with at least one example of the present disclosure.

FIG. 4 is a perspective view of the depth stop instrument 100 inserted into the intramedullary canal 302 of the bone 306, in accordance with at least one example of the present disclosure. In the illustrated example, the bone resection 304 is formed at the proximal end of the humerus bone 306, and the intramedullary canal 302 extends from the surface of the bone resection 304 into the humerus bone 306.

In the illustrated example, the instrument body 102 comprises an implant stem or a trial stem for use during procedures associated with shoulder replacement surgery. The implant stem or trial stem can be inserted into the intramedullary canal 302 until the bottom surface 210 of the ring 106 contacts the bone resection 304, preventing the implant stem or trial stem from inserting into the intramedullary canal 302 beyond a predetermined depth. Similar to that shown in FIG. 3, with the bottom surface 210 of the ring 106 resting on the surface of the bone resection 304, the ring 106 and the surface of the bone resection 304 share a common axis 308. The common axis 308 can be compared to an additional axis 310, such as a longitudinal axis of the instrument body 102, to measure an angle 312 of the ring 106 that can be used to approximate an inclination angle of the surface of the bone resection 304. In some examples, the inclination angle can be determined using the inclination indicator 112. In at least one example, the location of the ring 106 is compared to the inclination indicator 112 to determine the inclination angle of surface of the bone resection 304.

Figure 5:
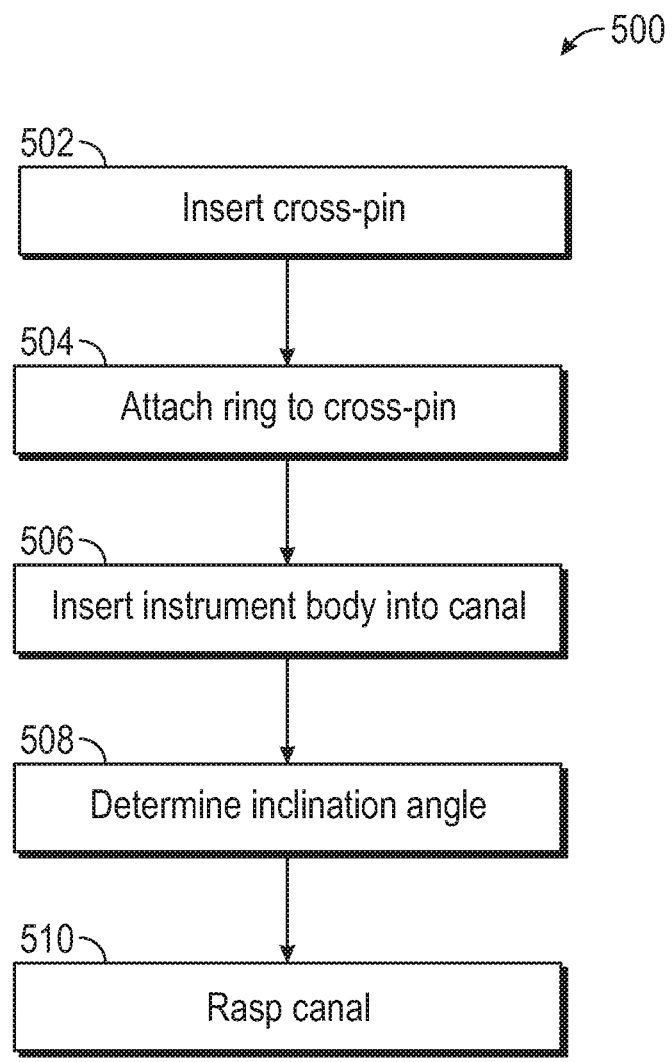
FIG. 5 is a flow chart of an example method of assembling and using the depth stop instrument of FIGS. 1-4, in accordance with at least one example of the present disclosure.

FIG. 5 is a flow chart 500 of an example method of assembling and using the depth stop instrument 100 in accordance with at least one example of the present disclosure. As a matter of convenience, the method 500 is described with reference to the depth stop instrument 100 of FIGS. 1-4. At block 502, a user can insert the cross-pin 104 through the opening 108 of the instrument body 102. In at least one example, the user can couple the cross-pin to the instrument body 102 using any of a variety of fasteners, for example, adhesive, solder, bolts, screws, or the like. In some examples, the user can threadably couple the cross-pin 104 to the instrument body 102 via corresponding threads 202, 204. In another example, the user can form the cross-pin 104 integral with the instrument body 102, rather than inserting the cross-pin 104 through an opening in the instrument body.

At block 504, the user attaches the ring 106 to the cross-pin 104. In at least one example, the user can couple the cross-pin 104 to at least one of the first portion 206 of the ring 106 and the second portion 208 of the ring 106. In some examples, the user can attach the ring 106 to the cross-pin 104 by coupling the first portion 206 of the ring 106 and the second portion 208 of the ring 106 over the cross-pin 104. In at least one example, the user can threadably couple the cross-pin 104 to the ring 106. In some examples, the user can form the ring 106 integral with the cross-pin 104. In at least one example, the user can attach the ring 106 to the cross-pin 104, such that the ring 106 encircles the instrument body 102. In some examples, the user can configure the ring 106 to pivot about the cross-pin 104. In other examples, the user can configure the ring 106 and the cross-pin 104 to rotate about the longitudinal axis 110 of the cross-pin 104. In some examples, the user receives the depth stop instrument 100 pre-assembled, such that the user performs the method 500 beginning at block 506.

At block 506, the user can partially insert the instrument body 102 into the intramedullary canal 302. In at least one example, the user can insert the instrument body 102 into the intramedullary canal 302 until the base 210 of the ring 106 contacts the surface of the bone resection 304, preventing the instrument body 102 from being inserted further into the intramedullary canal 302. At block 508, the user can determine an inclination angle of the surface of the bone resection 304. In at least one example, the user uses the angle 312 of the ring 106 relative to the instrument body 102 to approximate a surface angle of the bone resection 302. In some examples, the user utilizes an inclination indicator 112 in combination with the position of the ring 106 to determine an inclination angle associated with the surface of the bone resection 302. In some examples, the user can use the inclination angle to determine an appropriate head inclination for an implant. In some examples, the user does not determine the inclination angle, and instead the method 500 proceeds from inserting the instrument body 102 at block 506 to block 510. At block 510, the user can rasp the intramedullary canal 302 using the instrument body comprising the rasp handle 114 and the rasp 116. In some examples of the method 500, the user uses an instrument body 102 comprising an implant stem or a trial stem, and does not rasp the intramedullary canal 302 at block 510.

In the foregoing Detailed Description, it can be seen that various features are grouped together in a single example for the purpose of streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus the following claims are hereby incorporated into the Detailed Description, with each claim standing on its own as a separate example.

Note that not all of the activities or elements described above in the general description are required, that a portion of a specific activity or device may not be required, and that one or more further activities may be performed, or elements included, in addition to those described. Still further, the order in which activities are listed are not necessarily the order in which they are performed. Also, the concepts have been described with reference to specific examples. However, one of ordinary skill in the art appreciates that various modifications and changes can be made without departing from the scope of the present disclosure as set forth in the claims below. Accordingly, the specification and figures are to be regarded in an illustrative rather than a restrictive sense, and all such modifications are intended to be included within the scope of the present disclosure.

Benefits, other advantages, and solutions to problems have been described above with regard to specific examples. However, the benefits, advantages, solutions to problems, and any feature(s) that may cause any benefit, advantage, or solution to occur or become more pronounced are not to be construed as a critical, required, or essential feature of any or all the claims. Moreover, the particular examples disclosed above are illustrative only, as the disclosed subject matter may be modified and practiced in different but equivalent manners apparent to those skilled in the art having the benefit of the teachings herein. No limitations are intended to the details of construction or design herein shown, other than as described in the claims below. It is therefore evident that the particular examples disclosed above may be altered or modified and all such variations are considered within the scope of the disclosed subject matter. Accordingly, the protection sought herein is as set forth in the claims below.

What is claimed is:

1. An instrument, comprising:
   an instrument body configured to be partially inserted into an intramedullary canal of a bone having a bone resection;
   a cross-pin extending through and across the instrument body;
   a ring coupled directly to the cross-pin and positionable on the bone resection such that a portion of the ring is configured to contact a surface of the bone resection, the ring configured to pivot about a longitudinal axis of the cross-pin such that an angle of the ring relative to the instrument body approximates a surface angle of the bone resection relative to the instrument body; and
   an inclination indicator configured to indicate the surface angle of the bone resection when the ring is positioned on the bone resection.

2. The instrument of claim 1, wherein the instrument body comprises a rasp handle.

3. The instrument of claim 1, wherein the instrument body further comprises a rasp, such that the rasp is configured to be inserted into the intramedullary canal of the bone.

4. The instrument of claim 1, wherein the instrument body comprises an implant stem or a trial stem.

5. The instrument of claim 1, wherein the ring comprises a first portion and a second portion separable from the first portion, the first and second portions being configured for assembly on the cross-pin to form the ring.

6. The instrument of claim 1, wherein the ring comprises metal.

7. The instrument of claim 1, wherein the ring comprises plastic.

8. The instrument of claim 1, wherein the inclination indicator comprises markings on the instrument body.

9. The instrument of claim 1, wherein the instrument is a depth stop instrument for shoulder replacement surgery.

10. The instrument of claim 1, wherein the ring prevents the instrument body from being inserted into the intramedullary canal of the bone beyond a predetermined depth.

11. An instrument, comprising:
    an instrument body configured to be partially inserted into an intramedullary canal of a bone having a bone resection;
    a cross-pin extending through and across the instrument body;
    a ring attached directly to the cross-pin, the ring configured to rotate about a longitudinal axis of the cross-pin such that when a base surface of the ring contacts a surface of the bone resection, the instrument body is prevented from being inserted into the intramedullary canal of the bone beyond a predetermined depth; and
    an inclination indicator configured to indicate a surface angle of the bone resection when the ring is positioned on the bone resection.

12. The instrument of claim 11, wherein the instrument body comprises a rasp handle.

13. The instrument of claim 11, wherein the instrument comprises a depth stop system for shoulder replacement surgery.

14. The instrument of claim 11, wherein the ring is configured such that when the base surface of the ring contacts the surface of the bone resection, an angle of the ring relative to the instrument body approximates a surface angle of the bone resection relative to the instrument body.

15. The instrument of claim 11, wherein the ring is integral with the cross-pin, such that the cross-pin rotates about its longitudinal axis with the ring.

16. A method, comprising:
    inserting a cross-pin through an opening in an instrument body such that the cross-pin extends across and through the instrument body; and
    attaching a ring directly to the cross-pin such that the ring encircles the instrument body, the ring configured to pivot about the cross-pin such that an angle of the ring relative to the instrument body can approximate a surface angle of a bone resection relative to the instrument body when the instrument body is partially inserted in an intramedullary canal of a bone having the bone resection and the ring is positioned on the bone resection such that a portion of the ring contacts a surface of the bone resection and an inclination indicator indicates the surface angle of the bone resection when the ring is positioned on the bone resection.

17. The method of claim 16, wherein attaching the ring to the cross-pin comprises:
coupling a first portion of the ring to a second portion of the ring, and
coupling the cross-pin to at least one of the first portion and the second portion.

18. The method of claim 16, wherein inserting the cross-pin through the opening in the instrument body comprises threadably coupling the cross-pin to the instrument body.

19. The method of claim 16, wherein the comprises a method for making a depth stop instrument for shoulder replacement surgery.

* * * * *

UNITED STATES PATENT AND TRADEMARK OFFICE
CERTIFICATE OF CORRECTION

PATENT NO. : 10,874,407 B2  
APPLICATION NO. : 15/159069  
DATED : December 29, 2020  
INVENTOR(S) : Andrew Hopkins Page 1 of 1

It is certified that error appears in the above-identified patent and that said Letters Patent is hereby corrected as shown below:

In the Claims

In Column 8, Line 56, in Claim 16, delete "body" and insert --body,-- therefor

In Column 9, Line 12, in Claim 19, after "the", insert --method--

Signed and Sealed this
Twenty-third Day of March, 2021

Drew Hirshfeld
*Performing the Functions and Duties of the
Under Secretary of Commerce for Intellectual Property and
Director of the United States Patent and Trademark Office*